United States Patent [19]

Fake

[11] 3,973,023

[45] Aug. 3, 1976

[54] ANTI-HYPERTENSIVE POLYCYCLIC COMPOUNDS FOR TREATING HYPERTENSION

[75] Inventor: Charles Sylvester Fake, Harlow, England

[73] Assignee: Beecham Group Limited, England

[22] Filed: Oct. 22, 1974

[21] Appl. No.: 517,001

Related U.S. Application Data

[62] Division of Ser. No. 324,222, Jan. 10, 1973, Pat. No. 3,853,899.

[30] Foreign Application Priority Data

Jan. 26, 1972 United Kingdom.................. 3654/72

[52] U.S. Cl. .............................................. 424/263
[51] Int. Cl.² ........................................ A61K 31/44
[58] Field of Search ..................................... 424/263

[56] References Cited
UNITED STATES PATENTS 3,707,474 12/1972 Razdan et al..................... 260/295 F
3,726,883 4/1973 Razdan et al. .................. 260/297 B Primary Examiner—V. D. Turner
Assistant Examiner—Daren M. Stephens

[57] ABSTRACT

Chromanols of the formula (II)

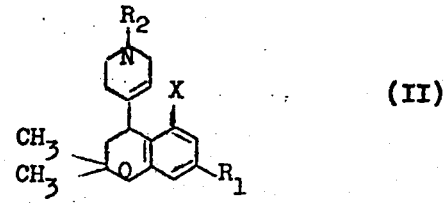

wherein $R_1$ is a non-aromatic hydrocarbon group of 1–20 carbon atoms, $R_2$ is a hydrocarbon group of 1–20 carbon atoms optionally substituted by a halogen atom and X is an optionally salted, etherified or acylated hydroxyl group, and N-oxides, acid-addition and quaternary salts thereof are shown to have antihypertensive activity. Their preparation and compositions containing them are described.

14 Claims, No Drawings

ANTI-HYPERTENSIVE POLYCYCLIC COMPOUNDS FOR TREATING HYPERTENSION

This is a division of application Ser. No. 324,222 filed Jan. 10, 1973, now U.S. Pat. No. 3,853,899 issued Dec. 10, 1974.

This invention relates to novel chromanols having a tetrahydropyridyl group in the 4-position, to processes for their preparation and to pharmaceutical compositions containing them. Compounds within the scope of the present invention have useful cardiovascular and central nervous system (CNS) activity, such as, for example, antihypertensive activity.

It is known that certain chromanols of general formula (I)

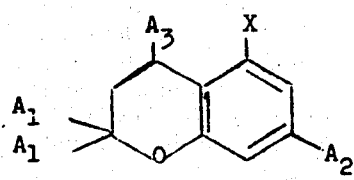

wherein $A_1$ is a hydrocarbon group of 1–6 carbon atoms, $A_2$ is a hydrocarbon group of 1–20 carbon atoms, $A_3$ is an optionally substituted aromatic or heteroaromatic group and X is a hydroxyl group optionally salted, acylated or etherified.

Certain compounds of general formula (I) have been shown to possess CNS activity. It has now been found that related compounds in which $A_3$ is a tetrahydropyridyl group have antihypertensive activity.

Accordingly the present invention provides chromanols of general formula (II):

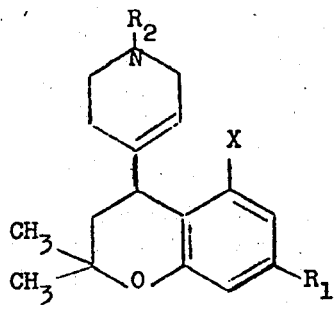

wherein $R_1$ is a non-aromatic hydrocarbon group of 1–20 carbon atoms, $R^2$ is a hydrocarbon group of 1–20 carbon atoms optionally substituted by a halogen atom and X is an optionally salted, etherified or acylated hydroxyl group; and N-oxides, acid-addition and quaternary salts thereof.

Suitable groups $R_1$ include straight or branched aliphatic groups such as the methyl, amyl, hexyl, heptyl, 2-hexyl, 2-heptyl, 2-octyl, 2-methyl-2-hexyl, 3-methyl-2-octyl, dodecyl and like groups.

Suitable groups $R_2$ include groups such as the methyl, 2-chloroethyl, 1-naphtylmethyl, 2-naphthylmethyl, benzyl and 2-phenyl ethyl.

Suitable groups X include the hydroxyl group optionally salted by an alkali metal ions such as the sodium or potassium ion or optionally acylated by groups such as the acetyl or β-diethylaminopropionyl groups or optionally etherified by optionally substituted hydrocarbon groups such as the methyl or α-dimethyl-amino propyl group.

A preferred group of compounds with general formula (II) are those of general formula (III):

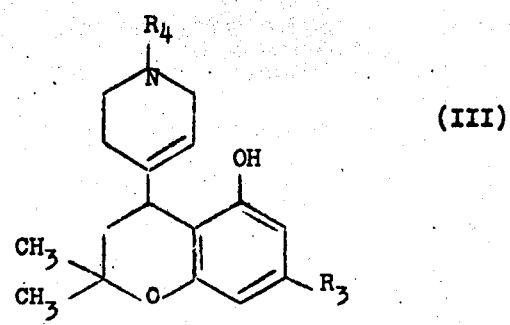

wherein $R_3$ is an alkyl group of 4–10 carbon atoms and $R_4$ is a hydrocarbon group of 7–12 carbon atoms, and salts thereof.

Preferred groups $R_3$ include the n-amyl, n-hexyl, 2-hexyl, 2-heptyl, 2-octyl, 2-methyl-2-hexyl and 3-methyl-2-octyl groups.

Preferred groups $R_4$ include the 2-propenyl, 2-phenylethyl, benzyl, 1-naphthylmethyl and 2-naphthylmethyl groups.

Compounds of the formula: (IV):

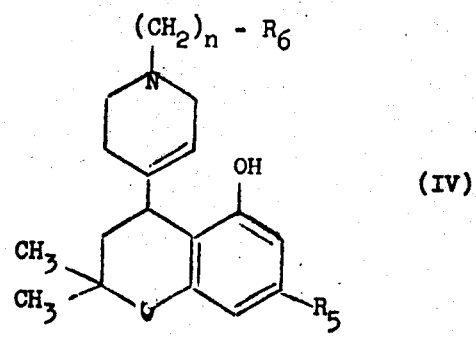

wherein $R_5$ is a $C_5$-$C_8$ alkyl group which is straight chained or branched at the α-carbon atom, $n$ is 1 or 2 and $R_6$ is phenyl or naphthyl, and salts thereof, are especially preferred as it is believed that such compounds combine useful anti-hypertensive activity with low mamalian toxicity.

In a second aspect the invention provides a process for the preparation of compounds of formula (II), said process comprising the reduction of a compound of formula (V):

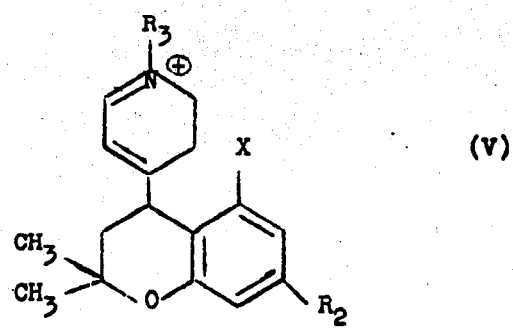

(wherein B⁻ represents an anion) with a borohydride and thereafter if desired replacing $R_3$ and/or X in known manner.

Generally X is a hydroxyl or salted hydroxyl group in compounds of formula (V). If the desired group X is an estherified or acylated hydroxyl group, this may be prepared by standard procedures after the reduction reaction has taken place.

Suitably the borohydride is an alkali metal borohydride, preferably $NaBH_4$.

The reaction generally takes place in a solvent such as an alcohol or aqueous alcohol, for example, aqueous ethanol or the like.

Any non-extreme temperatures may be used, the reaction time being shorter when higher temperatures are employed. Preferably the temperature is between 0° and 100°C, most preferably at room temperature.

Intermediates of formula (IV) are also novel and are included within the scope of the invention.

Certain chroman-5-ols may be subject to aerial oxidation when in solution. As a result it is often advantageous to prepare and isolate the compounds of the invention under an atomosphere of nitrogen.

Compounds (V) may be made by the quaternisation of the corresponding 4-pyridyl compound, for example, by reaction with an alkyl benzyl bromide, naphthylmethylbromide allyl chloride or the like.

In a further aspect, the invention provides a pharmaceutical composition useful in treating hypertension, said composition comprising a compound of formula (II) together with one or more pharmaceutical carriers. Such compositions may, if required, contain other antihypertensive agents and/or diuretics and may, if required, be made up in unit dosage forms.

Generally from 1–50 mg/kg/day of a compound of formula (II) may be administered.

The following Examples serve to illustrate the invention.

EXAMPLE 1

7-(n-Amyl)-4-(1-benzyl-1,2,5,6-tetrahydro-4-pyridyl)-2,2-dimethyl-chroman-5-ol 7-n-Amyl-2,2-dimethyl-4-(4-pyridyl)-chroman-5-ol (3.25 g., 0.01 mole) and benzyl bromide (1.88 g., 0.011 mole) were dissolved in acetone (50 ml) and the solution was refluxed for 4 hours. The solution was then concentrated to 0.5 volume and diethyl-ether was added until no further solid was precipitated. The precipitated solid (4.40 g) was filtered off and recrystallised from acetone/ethanol/ether to yield 1-benzyl-4-[7-(n-amyl)-2,2-dimethyl-5-hydroxy-chroman-4-yl]pyridinium bromide (d.24 g., 65%) as fawn microcrystals, m.p. 195°–200°.

This quaternary salt (3.12 g) was dissolved in a mixture of ethanol (40 ml) and water (15 ml) and the solution was stirred at ambient temperature whilst an excess of sodium borohydride (0.80 g) was added portionwise over 30 minutes. The resulting suspension was stirred for a further 30 minutes at ambient temperature and water (50 ml) was then added, followed by ether (100 ml). The organic layer was separated, washed with water (30 ml), dried over magnesium sulphate, and evaporated under reduced pressure to yield an orange oil (2.50 g). This crude product was dissolved in petroleum-ether (b.p. 60°–80°C) and the solution was filtered and cooled to −78°C to give 7-(n-amyl)-4)1-benzyl-1,2,5,6-tetrahydro-4-pyridyl)-2,2-dimethylcroman-5-ol (0.88 g., 33%) as colourless microcrystals, m.p. 63°–66°.

When dosed orally to groups of metacorticoid hypertensive rats at a dose of 100 mg/kg, the % fall in systolic blood pressure after 4 and 24 hours was 20% and 23% respectively [cf. 29% and 9% respectively for α-methyldopa].

EXAMPLE 2

7-(2-Hexyl)-2,2-dimethyl-4-[1-(2-phenylethyl)-1,2,5,6-tetrahydro-4-pyridyl]chroman-5-ol.

7-(2-Hexyl)-2,2-dimethyl-4-(4-pyridyl) chroman-5-ol (5.45 g, 0.016 mole) and 2-phenylethyl bromide (3.70 g, 0.020 mole) were dissolved in acetone (120 ml) and the solution was refluxed for 4 days. The solution was then allowed to cool and the resulting precipitate was filtered, washed with acetone and dried to yield 1-(2-phenylethyl)-4-[7-(2-hexyl)-2,2-dimethyl-5-hydroxychroman-4-yl]pyridinium bromide (7.22 g, 88%) as colourless microcrystals, m.p. 232°–235°C.

The quaternary salt (7.00 g) was dissolved in a mixture of ethanol (180 ml) and water (45 ml) and the solution was stirred at ambient temperature whilst an excess of sodium borohydride was added portionwise over 30 minutes. The resulting suspension was stirred for further 30 minutes at ambient temperature. Sufficient water and ether were then added to cause two phases to separate. The organic layer was separated, washed with water, dried ($MgSO_4$) and evaporated under reduced pressure to give a residual gum. Crystallisation from aqueous ethanol yield 7-(2-hexyl)-2,2-dimethyl-4-[1-(2-phenylethyl)-1,2,5,6-tetrahydro-4-pyridyl]chroman-5-ol (5.20 g., 85%) as colourless microcrystals, m.p. 141° – 143°C.

When dosed orally to groups of metacorticoid hypertensive rats at a dose of 100 mg/kg, the % fall in systolic blood pressure after 4 and 24 hours was 5% and 29% respectively [cf. 29% and 9% respectively for α-methyldopa].

EXAMPLES 3 – 5

Using procedures exactly analogous to those described in Examples 1 or 2 except that the reactions are carried out under nitrogen the following compounds may be prepared:

7-(n-Heptyl)-2,2-dimethyl-4-(1-benzyl-1,2,5,6-tetrahydro-4-pyridyl)-chroman-5-ol.

7-(n-Hexyl)-2,2-dimethyl-4-[1-(1-naphthylmethyl-1,2,5,6-tetrahydro-4-pyridyl)]-chroman-5-ol.

7-(2-Octyl)-2,2-dimethyl-4-[1-(2-naphythylmethyl-1,2,5,6-tetrahydro-4-pyridyl)]-chroman-5-ol.

We claim:

1. A pharmaceutical composition useful for treating hypertension in humans and animals which comprises an antihypertensively effective amount of a compound of the formula:

wherein $R_5$ is alkyl of 5 to 8 carbon atoms which is straight chained or branched at the α-carbon atom, n is 1 or 2 and $R_6$ is phenyl or naphthyl, or a pharmaceutically acceptable salt thereof, in combination with a pharmaceutically acceptable nontoxic inert diluent or carrier.

2. A pharmaceutical composition according to claim 1 wherein the compound is of the formula

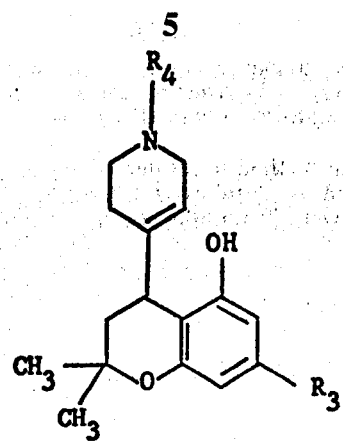

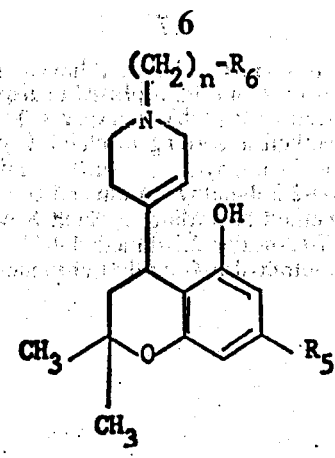

wherein R₃ is n-amyl, n-hexyl, 2-hexyl, n-heptyl, 2-heptyl, 2-octyl, 2-methyl-2-hexyl or 3-methyl-2-octyl, R₄ is 2-propenyl, 2-phenylethyl, benzyl, 1-naphthylmethyl or 2-naphthylmethyl, or a pharmaceutically acceptable non-toxic salt thereof.

3. A pharmaceutical composition according to claim 1 wherein the compound is of the formula

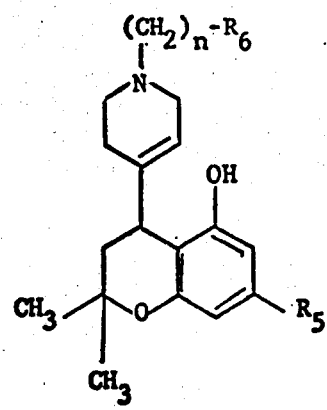

wherein $R_5$ is n-amyl, n-hexyl, 2-hexyl, n-heptyl or 2-octyl, $n$ is 1 or 2, and $R_6$ is phenyl or naphthyl, or a pharmaceutically acceptable nontoxic salt thereof.

4. The pharmaceutical composition according to claim 1 wherein the compound is 7-(n-amyl)-4-(1-benzyl-1,2,5,6-tetrahydro-4-pyridyl)-2,2-dimethyl-chroman-5-ol.

5. The pharmaceutical composition according to claim 1 wherein the compound is 7-(2-hexyl)-2,2-dimethyl-4-[1-(2-phenylethyl)-1,2,5,6-tetrahydro-4-pyridyl]-chroman-5-ol.

6. The pharmaceutical composition according to claim 1 wherein the compound is 7-(n-heptyl)-2,2-dimethyl-4-(1-benzyl-1,2,5,6-tetrahydro-4-pyridyl)-chroman-5-ol.

7. The pharmaceutical composition according to claim 1 wherein the compound is 7-(n-hexyl)-2,2-dimethyl-4-[1-(1-naphthylmethyl-1,2,5,6-tetrahydro-4-pyridyl)]-chroman-5-ol.

8. A method of treating hypertension in humans and animals which comprises administering to such human or animal an antihypertensively effective amount of a compound of the formula wherein $R_5$ is alkyl of 5 to 8 carbon atoms which is straight chained or branched at the α-carbon atom, $n$ is 1 or 2 and $R_6$ is phenyl or naphthyl, or a pharmaceutically acceptable salt thereof.

9. A method according to claim 8 wherein the compound is of the formula

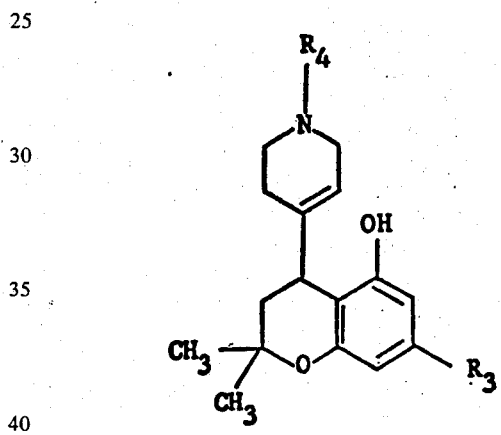

wherein R₃ is n-amyl, n-hexyl, 2-hexyl, n-heptyl, 2-heptyl, 2-octyl, 2-methyl-2-hexyl or 3-methyl-2-octyl, R₄ is 2-propenyl, 2-phenylethyl, benzyl, 1-naphthylmethyl or 2-naphthylmethyl, or a pharmaceutically acceptable nontoxic salt thereof.

10. A method according to claim 8 wherein the compound is of the formula

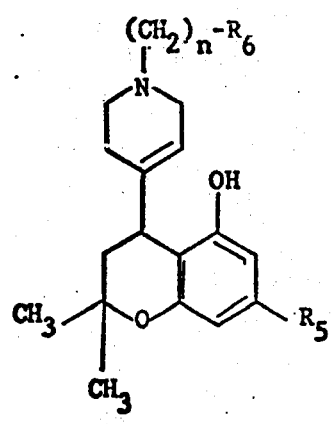

wherein $R_5$ is n-amyl, n-hexyl, 2-hexyl, n-heptyl or 2-octyl, $n$ is 1 or 2, and $R_6$ is phenyl or naphthyl, or a pharmaceutically acceptable nontoxic salt thereof.

11. The method according to claim 8 wherein the compound is 7-(n-amyl)-4-(1-benzyl-1,2,5,6-tetrahydro-4-pyridyl)-2,2-dimethyl-chroman-5-ol.

12. The method according to claim 8 wherein the compound 7-(2-hexyl)-2,2-dimethyl-4-[1-(2-phenylethyl)-1,2,5,6-tetrahydro-4-pyridyl]-chroman-5-ol.

13. The method according to claim 8 wherein the compound is 7-(n-heptyl)-2,2-dimethyl-4-(1-benzyl-1,2,5,6-tetrahydro-4-pyridyl)-chroman-5-ol.

14. The method according to claim 8 wherein the compound is 7-(n-hexyl)-2,2-dimethyl-4-[1-(1-naphthylmethyl-1,2,5,6-tetrahydro-4-pyridyl)]-chroman-5-ol.

* * * * *

UNITED STATES PATENT AND TRADEMARK OFFICE
CERTIFICATE OF CORRECTION

PATENT NO. : 3,973,023
DATED : August 3, 1976
INVENTOR(S) : CHARLES SYLVESTER FAKE It is certified that error appears in the above-identified patent and that said Letters Patent are hereby corrected as shown below:

Column 4, line 60, in claim 1 after "of the formula:", please insert the following structural formula:

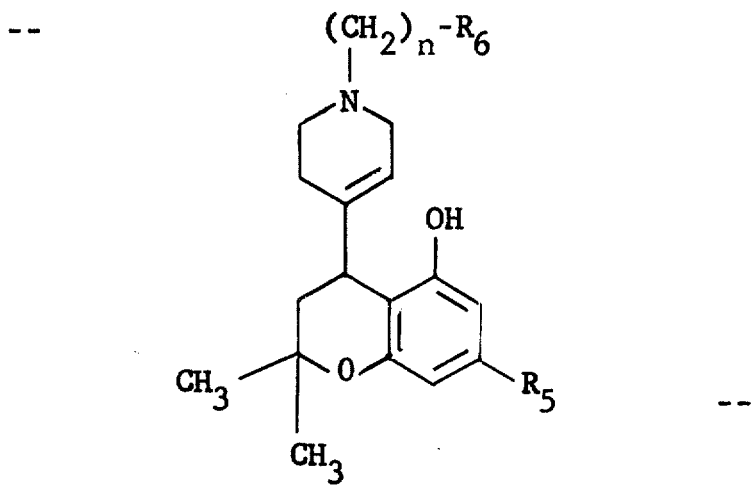

Signed and Sealed this

Nineteenth Day of October 1976

[SEAL]

Attest:

RUTH C. MASON
*Attesting Officer*

C. MARSHALL DANN
*Commissioner of Patents and Trademarks*